United States Patent [19]

Thompson

[11] 4,007,633
[45] Feb. 15, 1977

[54] METHOD OF DETERMINING THE PHYSICAL CHARACTERISTICS OF A SEA FLOOR
[75] Inventor: John R. Thompson, Camarillo, Calif.
[73] Assignee: The United States of America as represented by the Secretary of the Navy, Washington, D.C.
[22] Filed: Oct. 14, 1975
[21] Appl. No.: 621,714
[52] U.S. Cl. .................................. 73/84; 73/170 A
[51] Int. Cl.² ...................... G01N 3/30; G01N 3/48
[58] Field of Search ........... 73/84, 170 A; 340/3 D, 340/5 S

[56] References Cited
UNITED STATES PATENTS

| | | | |
|---|---|---|---|
| 3,298,222 | 1/1967 | Costello et al. | 73/84 |
| 3,341,808 | 9/1967 | Levin et al. | 73/170 A X |
| 3,455,151 | 7/1969 | Richard | 73/170 A X |
| 3,602,876 | 8/1971 | Gerard | 340/3 D X |

Primary Examiner—S. Clement Swisher
Attorney, Agent, or Firm—Richard S. Sciascia; Joseph M. St.Amand; Darrell E. Hollis

[57] ABSTRACT

A hollow, projectile-shaped body containing an acoustical transducer is released into the sea such that the body descends in free fall until it strikes and penetrates the sea floor, coming to a rest therein. Acoustic signals emanating from the acoustic transducer are processed utilizing the doppler effect to generate a direct current analog signal which is the function of the velocity of the body from a time immediately preceding the body striking the sea floor surface until the body comes to rest in the sea floor, thereby obtaining an indication of the physical characteristics of the sea floor.

4 Claims, 4 Drawing Figures

METHOD OF DETERMINING THE PHYSICAL CHARACTERISTICS OF A SEA FLOOR

BACKGROUND OF THE INVENTION

1. Field of the Invention

This invention relates generally to penetrometers and more specifically to such penetrometers utilizing the doppler effect.

2. Description of the Prior Art

Penetrometers have been used for years to gather technical information concerning sea floor characteristics. Prior art instrumentation utilized accelerometers, signal conditioning equipment, amplifiers and recorders which were packaged in single atmosphere enclosures attached to the accelometer. The cost of the instrumentation was high and it was necessary to recover the penetrometer and instrumentation package. This was done by attaching a load bearing cable to the vehicle to recover it after completion of its mission. This cable, capable of pulling the vehicle from the ocean bottom, produced drag as the vehicle fell toward the bottom which reduced its terminal velocity, thereby restricting its usefulness. Tape recorders, due to the high gravity forces encountered during deceleration are not capable of properly recording the data.

Another prior art method used the same costly instrumentation attached to an expendable penetrometer. Electrical analogs of the desired parameters are transmitted over a very small cable consisting of several wires. The breaking strength of this cable is one-half pound. It is spooled on two spools; one riding the vehicle and the other on the surface ship, both paying out cable simultaneously. Its success depended on the integrity (physical and electrical) of the spool cable. Electrically, the cable is basically a low pass distributed, constant, resistance-capacitance filter undesirable for the purpose of transmitting information from the penetrometer to the surface. Failure occurred due to breakage of the conductors in the environment.

SUMMARY OF THE INVENTION

The present invention is a method of determining the physical characteristics of a sea floor. One embodiment of the present invention utilizes an acoustical transmitter contained in a free falling penetrometer to transduce and transmit an electrical analog of the desired physical parameters of a sea floor to a surface receiver. By utilizing the heterodyne principle, the acoustic signal received from the acoustic transmitter translates the physical dynamics of the penetrometer as it penetrates the sea floor to an electrical analog of this data which, together with an appropriate time base, may be recorded on a magnetic tape, thus providing a permanent record of the desired dynamics of the penetrometer from a time immediately preceding the striking of the sea floor surface until the penetrometer comes to rest in the sea floor.

Accordingly, one object of the present invention is to provide a method of determining the physical characteristics of a sea floor.

Another object of the present invention is to provide both physical and electrical integrity.

A still further object of the present invention is to reduce cost while increasing efficiency.

One other object of the present invention is to increase reliability.

Other objects and a more complete appreciation of the present invention and its many attendant advantages will develop as the same becomes better understood by reference to the following detailed description when considered in connection with the accompanying drawings in which like reference numerals designate like parts throughout the figures thereof and wherein.

DETAILED DESCRIPTION OF THE PREFERRED EMBODIMENT

Figure 1:
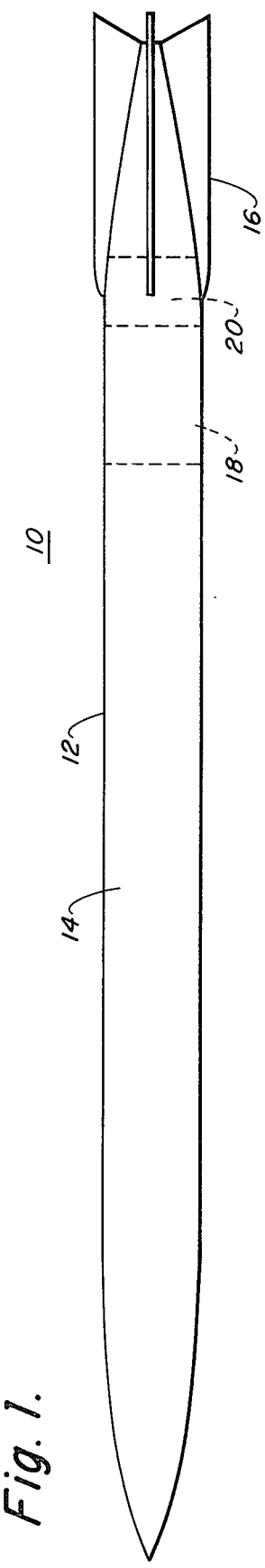
FIG. 1 is a side elevation illustrating one embodiment of the present invention.

FIG. 1 illustrates a projectile or penetrometer 10. Projectile 10 has an elongated body 12 of a known specific size, weight and shape. When released into the sea, body 12 falls freely. Its terminal velocity while in free fall as well as in other physical dynamics are known.

Body 12 contains body cavity 14. Attached to the end of body 12 is fin assembly 16. Fin assembly 16 contains four fins for stabilizing body 12 while body 12 is descending toward the sea floor.

Contained in body 12 is acoustic amplifier and battery power supply section 18 and acoustic transducer 20. Acoustic transducer 20 emits a constant frequency signal, e.g., 12 Kilohertz. Acoustic transducer 20 is disposed such that the acoustic signal emitted therefrom is directed upward toward the sea surface.

The projectile or penetrometer 10 is released near the surface of the sea and descends in free fall toward the sea floor. Upon striking the sea floor, the penetrometer 10 will penetrate into the sea floor and come to a rest therein.

The method of this invention utilizes the doppler principle to transduce the dynamic physical parameters of the sea floor from an apparent or doppler frequency shift. Penetrometer 10 in free fall carrys the transducer 20 away from a receiver located near the sea surface at an ever increasing rate until a terminal velocity has been reached. The apparent or doppler frequency shift which, in this case is negative with reference to 12 KHz, now will remain a constant until penetrometer 10 strikes the sea floor and begins to slow in velocity. As the penetrometer begins to slow in velocity, the apparent or doppler frequency shift is now in a positive direction toward 12 KHz, and when the vehicle comes to rest, the received frequency will be 12 KHz.

Figure 2:
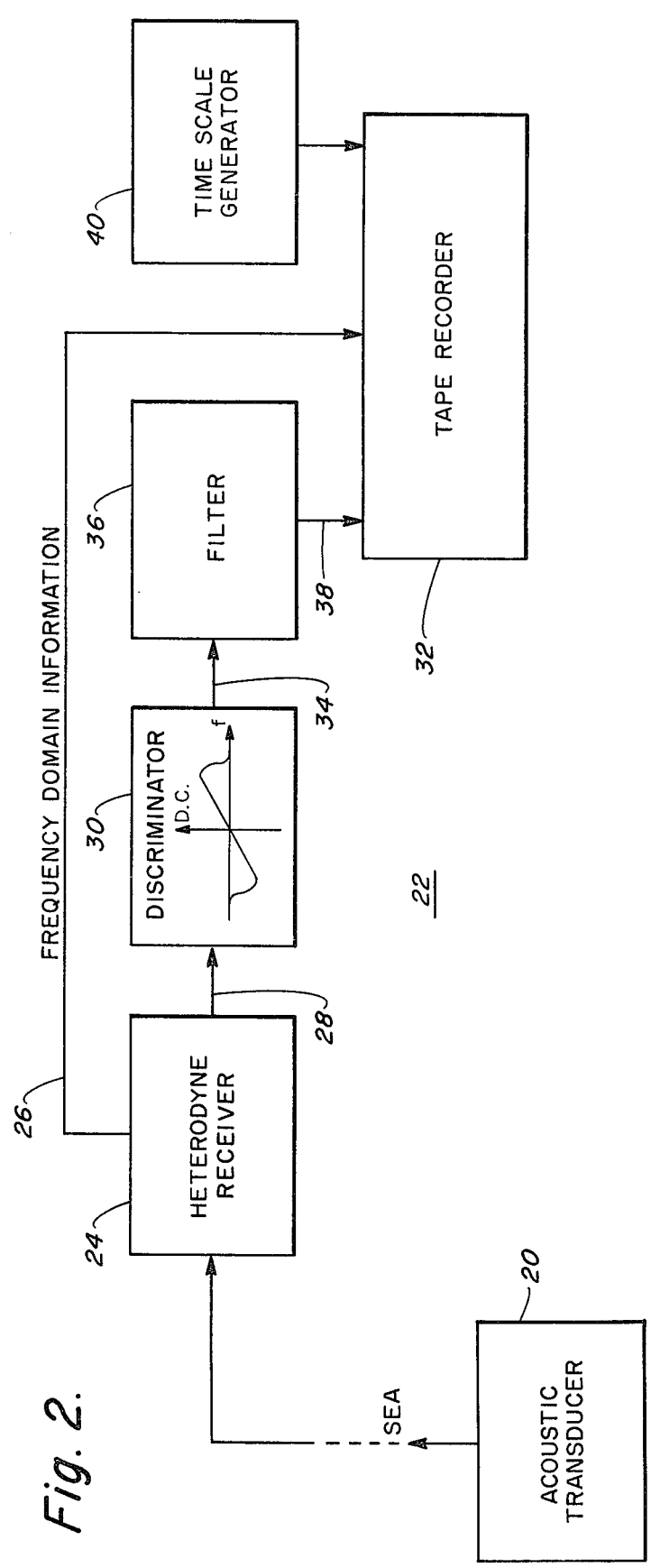
FIG. 2 is a schematic of the electrical acoustic signal processing equipment in one embodiment of the present invention.

Now turning to FIG. 2, signal processing equipment 22 is illustrated in schematic form. Acoustic transducer 20, located within hollow body 12, transmits a 12 KHz signal through the sea to heterodyne receiver 24. Of course, the signal received by receiver 24 is less than 12 KHz due to the doppler shift, as explained supra.

Heterodyne receiver 24 outputs a heterodyned signal on lines 26 and 28. Heterodyne receiver 24 has a bandwidth of approximately 11,500 to 12,500 Hz. It is noted that the specific frequencies disclosed herein are for the purpose of illustrating Applicant's invention and are not intended as the only or most desirable frequencies available. The heterodyned signal on lines 26 and 28 is between 4.5 and 4.8 KHz in frequency. The heterodyned signal on line 26 is directed to tape recorder 32. The heterodyned signal on line 28 inputs discriminator 30.

Discriminator 30 is a frequency-modulated discriminator having a center frequency of approximately 4.8 KHz whose output on line 34 is a direct current analog of the velocity, either positive or negative, of penetrometer 10. The direct current analog signal on line 34 is filtered via filter 36 and passed via line 38 to tape recorder 32.

Also, inputting tape recorder 32 is time scale generator 40.

Figure 3:
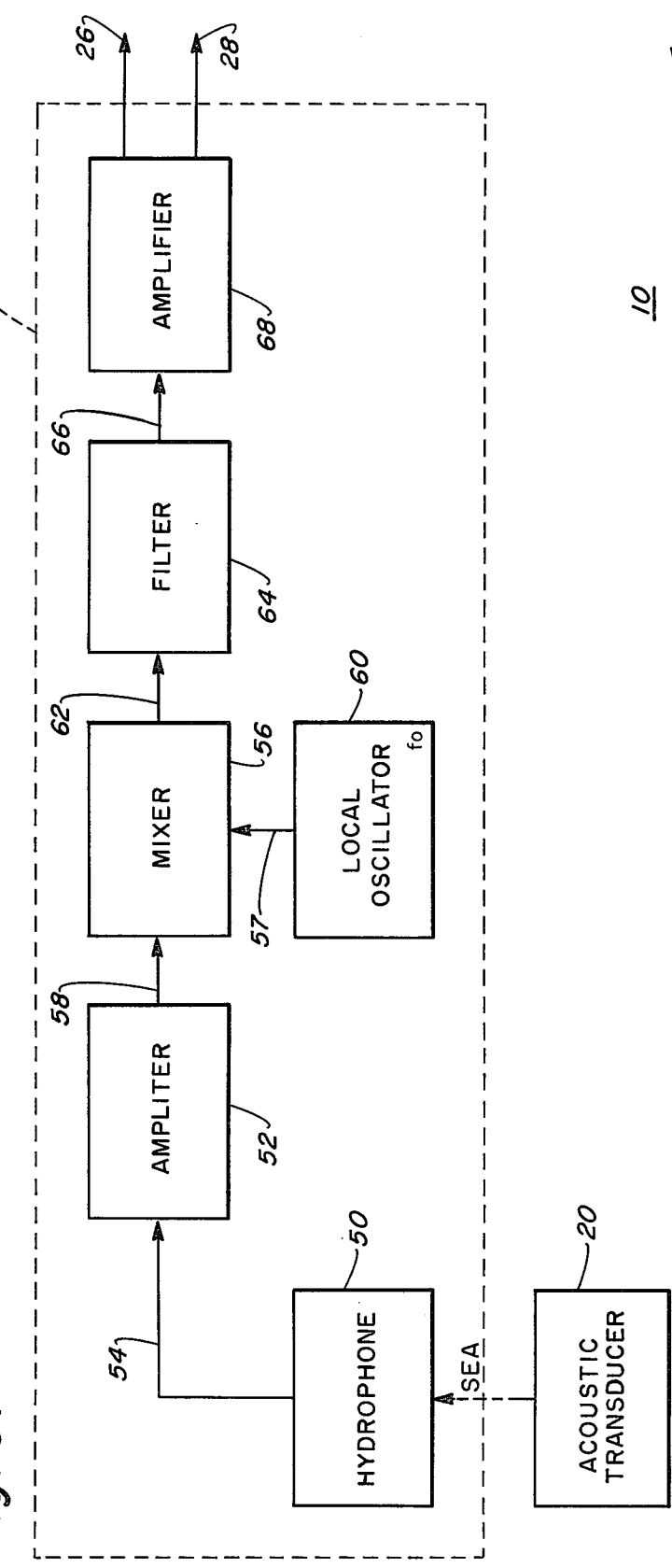
FIG. 3 is a schematic of the heterodyne receiver contained in the circuitry of FIG. 2.

Now turning to FIG. 3, heterodyne receiver 24 is shown in greater detail. Hydrophone 50 receives the acoustic signal transmitted from acoustic transducer 20 located in penetrometer 10. The signal from hydrophone 50 inputs amplifier 52 on line 54. The output of amplifier 52 inputs mixer 56 via line 58. Also, inputting mixer 56 on line 57 is a local oscillator signal from local oscillator 60. The A-C signal from local oscillator 60 has a specific frequency, $f_0$, e.g., 7.2 KHz. The output of mixer 56 on line 62 is a signal containing the sum and difference of the received signal on line 58 and the local oscillator signal $f_0$. A signal on line 62 is filtered in this case to eliminate the summed frequency by filter 64. The filter output signal on line 66 is then amplified by amplifier 68. Amplifier 68 had outputs 26 and 28 corresponding to outputs 26 and 28 of FIG. 2. Assuming, for example, that acoustic transducer 20 outputs a 12 KHz signal, local oscillator signal $f_0$ can be set at approximately 7.2 KHz, thereby causing an A-C signal of approximately 4.8 KHz to appear on lines 26 and 28. Of course, even though acoustic transducer 20 outputs a constant 12 KHz signal, due to the doppler effect the signal received by hydrophone 50 will be less than 12 KHz, as explained supra.

Assuming the received signal from acoustic transducer 20 is exactly 12 KHz, then the signal on line 66 will be 4,800 Hz. Discriminator 30 has a center frequency of approximately 4,800 Hz with a bandwidth of approximately 250 Hz on either side of the center frequency. Thus, heterodyne receiver 24 lowers the frequency of the information signal, thus providing greater sensitivity to the signal transmitted to tape recorder 32 via line 38 since the discriminator has only a 250 Hz bandwidth on eigher side of its center frequency.

Figure 4:
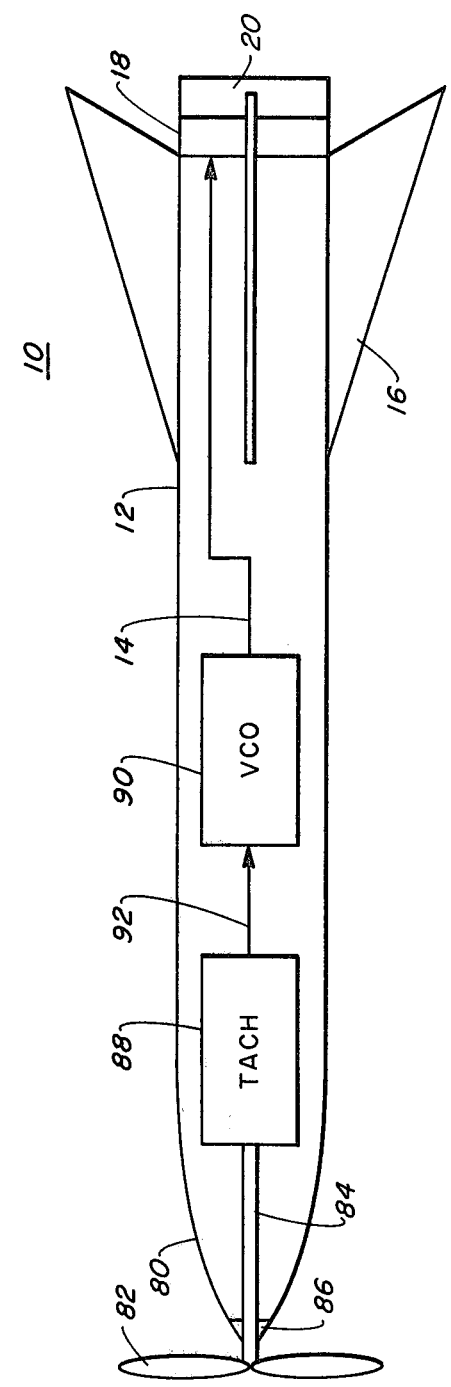
FIG. 4 is a side elevation of a second embodiment of the present invention.

Now turning to FIG. 4, penetrometer 10 is illustrated showing a further embodiment of the present invention. Penetrometer 10 is comprised of elongated body 12 having a hollow body cavity 14 therein. Fin assembly 16 is disposed near the rear of body 12. Contained in body 12 are acoustic amplifier and battery power supply section 18 and acoustic transducer 20. Located near nose section 80 of body 12 is impeller 82 which is attached to shaft 84. Shaft 84 extends from inside body cavity 14 to outside body cavity 14 where shaft 84 is rigidly affixed to impeller 82. Shaft 84 rotates with respect to body 12 about bearings 86. Shaft 84 mechanically inputs tachometer 88. Tachometer 88 outputs a DC signal which is functionally related to the rotation of impeller 82 as transmitted to tachometer 88 via shaft 84. The DC signal output from tachometer 88 inputs voltage control oscillator 90 via line 92. Voltage control oscillator 90 outputs an AC signal to acoustic amplifier 18. Of course, the frequency of the signal from voltage control oscillator 90 varies with the DC level of the signal inputing voltage control oscillator 90 on line 92. Thus, the frequency of the acoustical signal transmitted into the water by acoustic transducer 20 is functionally related to the speed of rotation of propeller 82, thereby giving an indication of the speed of body 12 through the water since the speed of rotation of impeller 82 is functionally related to the speed of body 12 through the sea.

It will be appreciated by those having ordinary skill in the art that the complete circuit diagram of FIGS. 2 and 3 includes such suitable and necessary calibration as is usually provided in such circuits, and the penetrometers of FIGS. 1 and 4 include such suitable and necessary water-proofing means as is usually provided in such devices.

Obviously numerous modifications and variations of the present invention are possible in light of the above teachings. It is therefore to be understood that within the scope of the appended claims the invention may be practiced otherwise than as specifically described herein.

What is claimed is:

1. A method of determining the physical characteristics of the sea floor comprising the steps of:
    a. providing a body of known size, weight, and shape capable of generating and transmitting acoustical signals;
    b. releasing said body into the sea such that said body descends in free fall until it strikes and penetrates the sea floor coming to rest therein;
    c. directing said acoustic signals substantially vertically upward from said body;
    d. receiving said acoustic signals in receivers disposed near the sea surface; and
    e. generating from said received acoustic signals, utilizing the doppler effect, a direct-current analog signal which is a function of the velocity of said body from a time immediately preceding said body's striking the sea floor surface until said body comes to rest in the sea floor, thereby obtaining an indication of the physical characteristics of the sea floor.

2. The method of claim 1 comprising the further step of recording said direct-current analog signal.

3. The method of claim 2 comprising the further steps of:
    a. generating a time scale signal; and
    b. recording said time scale signal in conjunction with said direct-current analog signal.

4. The method of claim 1 wherein said step of generating further comprises the steps of:
    a. heterodyning said received acoustic signals, thereby generating a heterodyned signal; and
    b. passing said heterodyned signal through a discriminator, thereby generating said direct-current analog signal.

* * * * *